United States Patent [19]

Okada et al.

[11] 4,211,769

[45] Jul. 8, 1980

[54] PREPARATIONS FOR VAGINAL ADMINISTRATION

[75] Inventors: Hiroaki Okada, Suita; Iwao Yamazaki; Takatsuka Yashiki, both of Takarazuka, all of Japan

[73] Assignee: Takeda Chemical Industries, Ltd., Osaka, Japan

[21] Appl. No.: 934,594

[22] Filed: Aug. 17, 1978

[30] Foreign Application Priority Data

Aug. 24, 1977 [JP] Japan .................................. 52-101945
Apr. 3, 1978 [JP] Japan .................................. 53-39337

[51] Int. Cl.² ............................................. A61K 37/00
[52] U.S. Cl. .................................................... 424/177

[58] Field of Search ............... 424/177; 260/112.5 CH

[56] References Cited

U.S. PATENT DOCUMENTS 3,917,825  11/1975  Matsuzawa et al. .................. 424/177

Primary Examiner—Frederick E. Waddell
Attorney, Agent, or Firm—Wenderoth, Lind & Ponack

[57] ABSTRACT

A preparation containing, as the main pharmaceutically active ingredient, a peptide having a luteinizing hormone-releasing hormone activity, is improved in its absorption by adding thereto a water-soluble aliphatic carboxylic acid of 2 to 6 carbon atoms.

9 Claims, No Drawings

PREPARATIONS FOR VAGINAL ADMINISTRATION

This invention relates to preparations for vaginal administration.

Vaginal suppositories containing a peptide having a luteinizing hormone-releasing hormone (hereinafter abbreviated as "LH-RH") activity have been disclosed, for example, in British Pat. No. 1393628 (corresponding to U.S. Pat. No. 3,917,825). While this known suppository comprises a composition obtained by dispersing a peptide having LH-RH activity in a mixture of an oleaginous base and a nonionic surfactant, we discovered that the incorporation of a certain type of watersoluble carboxylic acid in such a composition results in a surprisingly increased absorption of the active component into living body. This discovery was followed by further research which has culminated in the present invention.

Therefore, this invention relates to (1) a vaginal preparation containing a peptide having LH-RH activity and a water-soluble aliphatic carboxylic acid of 2 to 6 carbon atoms, (2) The vaginal preparation (1) consisting oleaginous base;

(3) The vaginal preparation (1) as an aqueous preparation, and (4) The vaginal preparation (1) wherein the peptide having LH-RH activity is one which has the following formula:

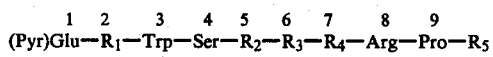

$$\overset{1}{(Pyr)Glu}-\overset{2}{R_1}-\overset{3}{Trp}-\overset{4}{Ser}-\overset{5}{R_2}-\overset{6}{R_3}-\overset{7}{R_4}-\overset{8}{Arg}-\overset{9}{Pro}-R_5 \quad (I)$$

[wherein $R_1$ means His, Tyr, Trp or p-$NH_2$-Phe; $R_2$ means Tyr or Phe; $R_3$ means Gly or a D-amino acid residue; $R_4$ means Leu, Ile, or Nle; $R_5$ means Gly-NH-$R_6$ ($R_6$ is H or a lower alkyl group having one to 3 carbon atoms which may optionally have a hydroxyl group) or NH-$R_6$ ($R_6$ is as defined above)].

The water-soluble aliphatic carboxylic acid of 2 to 6 carbon atoms, preferably of 3 to 6 carbon atoms, which is incorporated in the preparation of this invention may be any of the monocarboxylic acids, dicarboxylic acids, tricarboxylic acids, etc. The monocarboxylic acids include lower fatty aids, monocarboxylic acids having 1 to 5 hydroxyl groups, among others. The di- or tri-carboxylic acids may for instance be alkane-di- or tri-carboxylic acids (with 2 or 3 carboxyl groups attached to optional positions of an alkane chain.) Such alkane chains may be substituted in optional positions by hydroxyl and/or amino groups and the number of such hydroxyl groups is 1 to 3 and that of amino group is normally 1.

As examples of such carboxylic acids, there may be mentioned acetic acid, propionic acid, n-butyric acid, n-pentanoic acid, ascorbic acid, lactic acid, gluconic acid, glucuronic acid, malonic acid, succinic acid, citric acid, tartaric acid, malic acid, glutaric acid, adipic acid, aspartic acid, glutamic acid, etc. In the case of a polybasic acid, there are cases in which at least one of its carboxyl groups is free with the other carboxyl group or groups being in the form of an ester or salt. Among those water-soluble aliphatic carboxylic acids, succinic acid, tartaric acid, citric acid, etc. are particularly desirable for practical purposes.

The preparation according to this invention may be in any form that can be administered into the vagina. Thus, it may be used in any of such dosage forms as suppositories, ointments, tablets, aqueous solutions (includes one which is supported on solid matrixes), aqueous gels and emulsions.

The proper amount of such a water-soluble aliphatic carboxylic acid in many instances other than aqueous solutions is within the range of about 0.5 to 50 percent by weight and, preferably, within the range of about 2 to 20 percent by weight.

The amount of such water-soluble aliphatic carboxylic acid in the solutions can be selected from the range of about 0.5 to 20 percent by weight, preferably about 1 to about 10 percent by weight, depending on the intended use, based on the weight of the aqueous solution in the vaginal preparation according to this invention (e.g. an aqueous solution of the water-soluble aliphatic carboxylic acid, a peptide having LH-RH activity, pH regulator, aqueous gel base, gel stabilizer, preservative, etc.).

The peptide which is incorporated in the preparation of this invention may be any peptide having LH-RH activity and, for example, peptides having the following formula may be suitably incorporated.

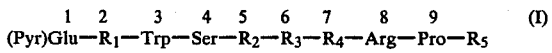

$$\overset{1}{(Pyr)Glu}-\overset{2}{R_1}-\overset{3}{Trp}-\overset{4}{Ser}-\overset{5}{R_2}-\overset{6}{R_3}-\overset{7}{R_4}-\overset{8}{Arg}-\overset{9}{Pro}-R_5 \quad (I)$$

[wherein $R_1$ means His, Tyr, Trp or p-$NH_2$-Phe; $R_2$ means Tyr or Phe; $R_3$ means Gly or a D-amino acid residue; $R_4$ means Leu, Ile or Nle; $R_5$ means Gly-NH-$R_6$ ($R_6$ is H or a lower alkyl group having one to 3 carbon atoms which may optionally have a hydroxyl group) or NH-$R_6$ ($R_6$ is as defined above)].

As examples of the D-amino acid residue $R_3$ there may be mentioned the residues of alpha-D-amino acids containing up to 9 carbon atoms (e.g. D-Leu, D-Ile, D-Nle, D-Val, D-Nval, D-Abu, D-Phe, D-Phg, D-Ser, D-Thr, D-Met, D-Ala, D-$\alpha$-Aibu, D-Trp, D-Tyr etc.), which may have suitable protective groups (e.g. t-butyl, t-butoxy, t-butoxycarbonyl, etc.). Of course, salts of peptide (I) with acids as well as metal complex compounds of peptide (I) may also be employed just as peptide (I). All abbreviations, wherever they are used in this specification to denote amino acids, peptides, protective groups, etc., are those according to IUPAC-IUB Commission on Biological Nomenclature or those commonly employed in the particular field of art. Where any of the amino acids named herein is subject to optical isomerism, all references to such amino acid mean the L-form unless otherwise indicated.

The following abbreviations are used, for instance:
Abu: $\alpha$-Aminobutyric acid
$\alpha$-Aibu: $\alpha$-Aminoisobutyric acid
Ala: Alanine
Arg: Arginine
Gly: Glycine
His: Histidine
Ile: Isoleucine
Leu: Leucine
Nle: Norleucine
Nva: Norvaline
Met: Methionine
Phe: Phenylalanine Phg: α-Phenylglycine
Pro: Proline
(Pyr)Glu: Pyroglutamic acid
Ser: Serine
Thr: Threonine
Trp: Tryptophan
Tyr: Tyrosine
Val: Valine
Bu$^t$: Tertiary butyl As the peptide having LH-RH activity known ones can be employed. Examples of those peptides are enumerated below;

(Pyr)Glu-His-Trp-Ser-Tyr-Gly-Leu-Arg-Pro-Gly-NH$_2$ (Pyr)Glu-His-Trp-Ser-Tyr-Gly-Leu-Arg-Pro-NH-C$_2$H$_5$ (Pyr)Glu-His-Trp-Ser-Tyr-D-Ala-Leu-Arg-Pro-NH-C$_2$H$_5$ (Pyr)Glu-His-Trp-Ser-Tyr-D-Ser(Bu$^t$)-Leu-Arg-Pro-NH-C$_2$H$_5$ (Pyr)Glu-His-Trp-Ser-Tyr-D-Leu-Leu-Arg-Pro-NH-C$_2$H$_5$ (Pyr)Glu-His-Trp-Ser-Tyr-Gly-Leu-Arg-Pro-NHCH$_2$CH$_2$OH (Pyr)Glu-His-Trp-Ser-Tyr-Gly-Leu-Arg-Pro-NHCH$_3$ (Pyr)Glu-His-Trp-Ser-Tyr-Gly-Leu-Arg-Pro-Pyrrolidine (Pyr)Glu-His-Trp-Ser-Tyr-Gly-NLe-Arg-Pro-NHC$_2$H$_5$ (Pyr)Glu-His-Trp-Ser-Phe-Gly-Leu-Arg-Pro-NHC$_2$H$_5$ (Pyr)Glu-His-Trp-Ser-Phe-Gly-Ile-Arg-Pro-NHC$_2$H$_5$ (Pyr)Glu-His-Trp-Ser-Tyr-Gly-Met-Arg-Pro-NHC$_2$H$_5$ The above peptides are described, for example, in U.S. Pat. No. 3,853,837 (corresponding to Belgium Pat. No. 798,114, DT-OLS 2,321,174, Netherland Pat. No. 7,305,995), Belgium Pat. No. 817,989 (corresponding to DT-OLS 2,435,027, Netherland Pat. No. 7,410,026), U.S. Pat. No. 4,008,209 (corresponding to Belgium Pat. No. 820,451, DT-OLS 2,446,005, Netherland Pat. No. 7,412,837) or U.S. Pat. No. 3,972,859 (corresponding to Belgium Pat. No. 826,430, DT-OLS 2,509,783, Netherland Pat. No. 7,502,564). [Note: "DT-OLS" means laying open specification in West Germany; "Netherland" means laying open specification in the Netherland.].

The amount of the peptide having LH-RH activity employed in the composition varies, however, it should be sufficient to ensure the desired pharmacological action. Thus, in many cases, it may be selected from the range of about 0.000025 to 10 percent by weight based on the composition of this invention. When ovulation stimulation is the expected action, it may sometimes be selected from the range of about 0.000025 to 1 percent by weight, preferably from about 0.0001 to 0.2 percent by weight, more preferably from about 0.0001 to 0.1 percent by weight. When an antitumor effect on breast cancer is desired, it may sometimes be selected from the range of about 0.001 to 20 percent by weight, preferably from about 0.01 to 10 percent by weight, and more preferably from about 0.01 to 5 percent by weight.

The preparation according to this invention can be prepared by established pharmaceutical procedures.

The preparation employable according to this invention include, among others, vaginal suppositories which remain solid at room temperature but melt at body temperature, ointments as dispersed in oily vehicles which are always liquid and gel type preparations which are administered through tube or the like. A further alternative form may be a preparation which, after vaginal application, would dissolve or disintegrate in vaginal fluids. Such a preparation can be easily administered, preferably by means of an applicator or inserter.

To prepare a vaginal suppository or ointment, the aforementioned carboxylic acid is dissolved or dispersed as fine powders in a previously melted oleaginous base and, then, a peptide having LH-RH activity is added and stirred at a suitable elevated temperature until a homogeneous dispersion is produced. This melted mass is then molded into dosage units. An alternative procedure, which is also known per se in the art of production of suppositories and ointments, comprises dispersing said organic acid in said base, dispersing an aqueous solution of said LH-RH-active peptide evenly in the melt and molding the resultant dispersion.

In this invention, any of the known ointment or suppository bases can be employed. Thus, polyethylene glycol bases may be mentioned as examples of water-soluble bases. Particularly desirable are those with degrees of polymerization not less than 100. For examples, those having the degrees of polymerization of 200, 300, 400, 1000, 4000, 6000, etc. may be mentioned. These bases may be used either alone or as a mixture. As examples of said oleaginous bases there may be mentioned such oils and fats as sesame oil, olive oil, corn oil, soybean oil, cottonseed oil, peanut oil, cacao butter, castor oil, laurin, beef tallow, lard, wool fat, turtle oil, squalene, etc., the corresponding modified materials as modified by such procedures as hydrogenation, fatty acid interchange, acetylation, fractional extraction, etc.; mineral oils such as vaseline, paraffin, isopar, silicone oil, etc.; glycerin esters of fatty acids of 6 to 30 carbon atoms, particularly higher fatty acid esters such as glycerin palmitate, glycerin laurate, glycerin stearate, glycerin myristate, etc.; esters of fatty acids of 6 to 30 carbon atoms with alcohols of 2 to 8 carbon atoms, particularly waxes such as isopropyl myristate, butyl stearate, diisopropyl adipate, diethyl sebacate, etc.; and higher fatty acids of 6 to 30 carbon atoms, particularly stearic acid, oleic acid, etc.

Such oleaginous bases may be used either alone or as a mixture. Particularly desirable oleaginous bases are corn oil, cacao butter and fatty acid-interchanged oils (e.g. mono-, di- and triglycerides of palmitic acid, stearic acid and other higher fatty acids).

To prepare vaginal tablets, the active component is compressed into appropriate dosage units generally by a procedure analogous to the known procedure, using diluent such as lactose, sucrose, starch, etc., disintegrating agents such as starch, sodium hydrogen carbonate, etc.; binders such as starch, gelatin, carboxymethyl-cellulose, polyvinylpyrrolidone, hydroxypropyl-cellulose, etc.; lubricants such as talc, magnesium stearate, polyethylene glycol (6000), stearic acid, etc. Where the required dosage is very small, an increased product uniformity may be obtained by preparing a mixed solution of a peptide having LH-RH activity with an excipient such as lactose, starch or mannitol beforehand then drying the mixed solution by way of freeze-drying or spray-drying to make a diluted powder and molding this diluted powder into tablets. In view of the relative scarcity of vaginal fluids as compared with gastrointestinal fluids disintegration and dissolution are important considerations.

To assist in disintegration and dissolution, there may be prepared effervescent tablets with the aid of sodium hydrogen carbonate and tartaric acid.

The aqueous vaginal preparation according to this invention can be prepared by established pharmaceutical procedures.

In the case of an aqueous solution, the peptide having LH-RH activity and said water-soluble aliphatic carboxylic acid containing 2 to 6 carbon atoms can be dissolved in an optional order. This aqueous solution must be acidic and, preferably, within the range of pH about 2 to about 6. The aqueous vaginal composition made up of the indicated amounts of peptide and water-soluble aliphatic carboxylic acid plus water may have a pH value within the above range but, if it does not, the composition is adjusted to a desirable pH within the range by means of a suitable acid, base, buffer or the like. As examples of the acid that may thus be employed for pH adjustment, there may be mentioned water-soluble aliphatic carboxylic acids of 2 to 6 carbon atoms, which as a class are a component of the composition of this invention, and inorganic acids. As examples of said base there may be mentioned sodium hydroxide and potassium hydroxide. As examples of said buffer, there may be mentioned Sörensen buffer (Ergeb. Physiol. 12, 393 (1912), Clark-Lubs buffer (J. Bact. 2, (1), 109, 191 (1971), MacIlvaine buffer (J. Biol. Chem. 49, 183 (1921), Michaelis buffer (Die Wasserstoffionenkonsentration, p 186 (1914), Kolthoff buffer (Biochem. Z. 179, 410 (1926) and so forth.

When the aqueous vaginal preparation is a water-soluble gel suppository, it can be prepared by mixing said water-soluble aliphatic carboxylic acid of 2 to 6 carbon atoms, said peptide having LH-RH activity, water and a gel base in a manner that is well established for the production of aqueous vaginal suppositories. As examples of the water-soluble gel bases, there may be mentioned naturally occurring gums (e.g. gum tragacanth, gum acacia, karaya gum, Irish moss, gum guaiac, gum xanthane, locust-bean gum, etc.), cellulose derivatives (e.g. methyl-cellulose, carboxymethylcellulose, etc.), acrylic acid polymers (e.g. polyacrylic acid, polymethacrylic acid, etc.), vinyl polymers (e.g. polyvinyl pyrrolidone, polyvinyl alcohol, polyvinyl methyl ether, carboxypolymethylene, etc.), synthetic polysaccharides (e.g. polysucrose, polyglucose, polylactose, etc.), starch, dextrin, pectin, sodium alginate and so forth. These bases may be employed either singly or, if necessary, as a mixture of two or more different bases and copolymers of the polymer mentioned above are also employed.

The water-soluble gel suppository may be prepared, for example in the following manner. Thus, an aqueous solution containing a water-soluble aliphatic carboxylic acid of 2 to 6 carbon atoms is first prepared and pH regulators, preservatives and other necessary components are then added. This solution is divided into two portions and the gel base is then dispersed or dissolved in one of the portions which is then heated or cooled as required to prepare a stable gel. In the other portion of said solution is dissolved the peptide having LH-RH activity. The two portions are evenly admixed, whereupon the desired water-soluble gel suppository is obtained.

The aqueous solution according to this invention can also be vaginally administered as supported on a solid matrix, for instance.

The solid matrix may be one of the known matrixes such as porous materials made of high molecular compounds (e.g. silicon rubber, polyurethane, etc.), biological polymers (e.g. collagen, hyaluronic acid, etc.), cellulosic materials e.g. cotton, paper, etc.) and so forth. After the aqueous solution has been supported on such a solid matrix, the matrix is dried to remove the water. As the medicated matrix is administered intravaginally, the active component is released under the influence of the vaginal fluids.

The aqueous solution of this invention may also be administered after it has been made into an oil-in-water or water-oil-water emulsion in the conventional manner with the aid of a suitable surfactant such as Span®, Arlacel® (higher fatty acid sorbitan ester, Atlas Powder Co.), Tween® (polyoxyethylene sorbitan fatty acid ester, Atlas Powder Co.), Pluronic® (polyoxypropylene-polyoxyethylene, Windot Co.), Brij® (polyoxyethylene alkyl ether, Atlas Powder Co.), lecithin, oils and fats (e.g. sesame oil, corn oil, rape oil, olive oil, peanut oil, cottonseed oil, oleic acid, linolic acid, etc.).

The aqueous solution according to this invention may also be administered in an aerosol foam.

If necessary, the aqueous vaginal preparation according to this invention may further contain other suitable components such as electrolytes (e.g. sodium chloride, potassium chloride, sodium carbonate, magnesium sulfate, etc.), wetting agents (e.g. glycerin, propylene glycol, sorbitol, etc.), preservatives (e.g. methylparaben, propylparaben, chlorobutanol, benzyl alcohol, sorbic acid, etc.), antioxidants (e.g. butylhydroxyanisole, sodium hydrogen sulfite, nordihydroguaiaretic acid, etc.) and so forth.

The single dosage of the vaginal preparation according to this invention may vary with the dosage form, the particular aspects of active component, animal species (e.g. mouse, rat, horse, cattle, man or other warm-blooded animal) to which the preparation is administered and the object of administration. At any rate, the dosage should only be sufficient to be pharmacologically effective and can be selected from the range of, for example, about 1 mg to about 500 mg of the final preparation per kilogram body weight. Although the proper number of doses per day may also vary the same way, it may be selected from the range of once to about 3 times a day.

The antitumor effect of the peptide is known, for example, in Science 194, 329 (1976), Cancer Research 36, 3830 (1976), U.S. Pat. No. 4,002,738.

The vaginal preparation according to this invention has the following and other advantageous features:

(1) In the vaginal administration of a peptide having LH-RH activity, there are cases in which the vaginal preparation of this invention induces ovulation even at low concentration which would not make for ovulation by the conventional preparations.

(2) In the vaginal administration of a LH-RH-active peptide for the stimulation of ovulation, this aqueous vaginal preparation, which is acid and contains the specified organic acid, induces ovulation effectively in a reduced peptide concentration and with the addition of only a small amount of said organic acid.

(3) The administration of an active derivative of LH-RH having antitumor activity against breast cancer, uteral cancer, etc., in the form of a vaginal preparation containing the specified water-soluble carboxylic acid according to this invention produces the desired antitumour effect at reduced peptide concentrations.

(4) In the vaginal dosage form according to this invention, various pharmacological effects such as relief from amenorrhea, dysmenorrhea, hypophyseoprivus or post-coital contraception by implantation inhibition, for instance, can be easily obtained with a reduced amount of LH-RH-active peptide, In the prior art, comparable effects have been obtainable only by multiple, frequent injections.

(5) Even when an antitumour action which would require multiple injections is desired, the vaginal preparation according to this invention enables the patient to administer it for herself, thus making home therapy possible.

(6) Particularly when it is aqueous, the vaginal preparation according to this invention has a high affinity for vaginal mucous membrane, permits ready pH adjustment and makes it easy to clean the implement and vagina after each administration. Moreover, because the components have been previously dissolved, there is neither burning nor irritation to the vaginal mucosa. Moreover, because each dosage unit is made up of reduced amounts of suppository base and other components, there is only a minor amount of residue in the vaginal tract.

(7) Compared with parenteral preparations, the serum levels of LH (luteinizing hormone; hereinafter abbreviated as "LH") and FSH (follicle stimulating hormone) following a vaginal administration can be maintained for a significantly extended time.

EXAMPLE 1

8 g of higher saturated fatty acid triglyceride (Witepsol ® S55; Dynamic Novel Aktiengesellschaft, West Germany; saturated vegitable fatty acid triglyceride containing a minor amount of monoglyceride) was melted at 50° C. and 1 g of milled succinic acid was added. After mixing well, 1 g of Witepsol ® S55 containing 2 mg of natural type LH-RH having the formula (Pyr)Glu-His-Trp-Ser-Tyr-Gly-Leu-Arg-Pro-Gly-NH$_2$ as previously dispersed therein was added. While it was warmed and agitated, the composition was filled into suppository containers for rats, 50 mg per container, which were then quenched in ice-water. By this procedure there were obtained suppositories. Incidentally the peptide having LH-RH activity content of each suppository can be adjusted either by increasing the concentration of the LH-RH in the separately prepared Witepsol ® S55 or by adding an increased amount of the same base with carboxylic acids to a base containing LH-RH.

EXAMPLE 2

In about 0.5 ml of water was dissolved 71.4 mg of the peptide having the formula (Pyr)Glu-His-Trp-Ser-Tyr-D-Leu-Leu-Arg-Pro-NH-C$_2$H$_5$ followed by addition of 4 g of lanolin. The mixture was homogenized well. Then, a mixture of 91 g of higher fatty acid triglyceride (Witepsol ® S55) pre-melted at 50° C. and 5 g of finely milled citric acid was gradually added with agitation. The composition was molded in plastic suppository containers, 1.4 g per container to prepare vaginal suppositories for human use, each suppository containing 1 mg of the peptide.

EXAMPLE 3

In 40 ml of water were dissolved and dispersed 2 mg of peptide having the formula (Pyr)Glu-His-Trp-Ser-Tyr-D-Leu-Leu-Arg-Pro-NH-C$_2$H$_5$ and 5 g of lactose and the solution was freeze-dried. The dried mixture was milled and 1 g was taken. To this was added 6.175 g of lactose, followed by mixing. Then, 1 g of citric acid and 1 g of corn starch were added. Then, 2 ml of a previously prepared 10% ethanolic solution of HPC (hydroxypropylcellulose) was added and admixed. The mixture was sieved, granulated and dried at 50° C. for 8 hours. The granules were then admixed well with 500 mg of corn starch and 125 mg of magnesium sterate, and 50 mg portions are tabletted. By the above procedure were obtained dissolution-type vaginal tablets for rats, containing 2 μg of the peptide per tablet.

EXAMPLE 4

According to the above Example 1, various amounts of natural type LH-RH namely having the formula (Pyr)Glu-His-Trp-Ser-Tyr-Gly-Leu-Arg-Pro-Gly-NH$_2$ were dispersed in an oleaginous base (Witepsol ®), in which 10% of citric acid had been dispersed in a state of fine particles as well as in a similar oleaginous base which contained no carboxylic acid. The resultant preparations were vaginally administered to rats to assess the ovulation-stimulating effects.

Diestrous female SD rats (120–150 days, body weights 250–350 g) were vaginally dosed and on the next day, autopsied to see if ovulation had taken place based on the presence or absence of ova in the ampulla.

The results are shown in Table 1.

Table 1

| Additives | \multicolumn{9}{c}{Dose of natural type LH-RH(ng/rat)} | ED$_{50}$ (95% fiducial limits) (ng/rat) |
|---|---|---|---|---|---|---|---|---|---|---|
| | 400 | 600 | 800 | 1,000 | 10,000 | 20,000 | 40,000 | 60,000 | 80,000 | |
| None | | | | | 1/10 | 2/10 | 10/10 | 9/10 | 10/10 | 24400 (17300–32100) |
| Citric acid (10%) | 1/10 | 1/10 | 4/10 | 8/10 | 4/4 | | | | | 820(680–1140) | n/n: The number of ovulating rats/the number of vaginally dosed rats.

EXAMPLE 5

By the similar procedure described in Example 1, a synthetic peptide having the formula (Pyr)Glu-His-Trp-Ser-Tyr-D-Leu-Leu-Arg-Pro-NH-C$_2$H$_5$ was dispersed in aliquots of an oleaginous base (based on glyceryl trilaurate) in which various organics acids had been respectively incorporated. A test for ovulation induction by the vaginal route was performed in the same manner as Example 4.

The results are set forth in Table 2.

Table 2

| Carboxylic acids | Dose (ng/rat) | | | | | | | | | | ED$_{50}$ (ng/rat) |
|---|---|---|---|---|---|---|---|---|---|---|---|
| | 20 | 40 | 60 | 80 | 100 | 150 | 200 | 400 | 600 | 800 | |
| None | | | | | 0/10 | | 3/10 | 8/10 | 9/10 | 10/10 | 270(194–353)* |
| Citric acid (10%) | | 2/10 | 6/10 | 8/10 | 9/10 | | 10/10 | 10/10 | 5/5 | 5/5 | 56(38–69)* |
| Succinic acid (10%) | 0/10 | 4/10 | 6/10 | 8/10 | 9/10 | | | | | | 50(37–63)* |
| Tartaric acid (10%) | | | 1/10 | 5/10 | 8/10 | 5/5 | | | | | 82(69–97)* |
| Aspartic acid (10%) | | | | 2/10 | 4/10 | | 9/10 | 9/10 | 10/10 | 5/5 | 122(79–169)* |
| Glutamic acid (10%) | | | | | 0/10 | | 7/10 | 10/10 | 10/10 | 5/5 | 177(133–243)* |
| Lactic acid (2%) | | | 2/10 | 0/10 | 3/10 | 8/10 | | | | | 117(95–184)* |
| Ascorbic acid (10%) | | | 3/10 | 2/10 | 4/10 | 7/10 | | | | | 114(80–161)* |

*95% fiducial limits
n/n: The number of ovulating rats/the number of vaginally dosed rats.

EXAMPLE 6

The same peptide as that described in Example 5 was dispersed in an oleaginous base composed predominantly of glyceryl trilaurate and supplemented with 10% of citric acid, and the resultant vaginal suppositories were continuously administered into the vaginas of six female rats in which breast cancers had been previously induced by oral administration of DMBA (7.12-dimethylbenzanthracene) to investigate and evaluate the antitumor effects. Thus, 350 μg/rat of the peptide was dispersed in 50 mg of suppository base and four animals were dosed every day except Saturdays and Sundays over a period of 2.5 months. As control, 2 rats were dosed with 100 μg/kg of the peptide as dissolved in physiological saline, subcutaneously in the same regimen as above.

The results showed that whereas a moderate growth inhibition of the tumours was obtained in both cases by the subcutaneous route, moderate inhibition was noted in 3 out of the four vaginally administered animals and a complete disappearance of the tumours was obtained in the remaining animal.

In all cases, an atrophy of the uterus and ovary probably attributable to the peptide administered was observed. In the case of cancers, effects of medication are difficult to assess quantitatively because of the involvement of various factors such as the stage of cancer, dosage level, frequency of administration, etc.

However, the results of this experiment indicate significant antitumour effects, showing satisfactory absorption.

As will be understood from the results of Example 4, 5 and 6, the incorporation of an organic acid such as citric acid results in a significantly increased absorption from the vagina of peptides having LH-RH activity.

In terms of ovulation-stimulating action, a 30 times increase of stimulating effect was obtained over the control (without carboxylic acid) in the case of natural type LH-RH (Table 1). As regards the synthetic peptide used in Example 5, the incorporation of 10% of succinic acid resulted in 5.4 times greater absorption than it was the case with the control (without organic acid). It is clear that a given pharmacological effect can be obtained at a dose equivalent to 5.2 times the intravenous dose or 3.1 times the subcutaneous dose. Incidentally, to achieve a given pharmacological effect by the oral administration of the same compound, a dose 1900 times as high as the intravenous dose is required and, in the absence of an carboxylic acid, as shown in Table 2, a dose 26 times as great as the intravenous dose must be administered when the vaginal route is selected. In view of these facts, it is obvious that the vaginal administration according to this invention is a very advantageous method of medication.

In terms of antitumour activity, while it is true that such complicating factors as the stage of the cancer, dosage and frequency of administration are involved, effective responses were obtained in 3 out of the five cases and a very effective response (disappearance of tumors) was obtained in one case.

Thus, the incorporation of a carboxylic acid has permitted treatment of cancers with reduced amounts of the peptide having LH-RH activity and by an expedient procedure, i.e. vaginal administration, which can be followed by the patients themeselves. This is a considerable contribution to the therapeutic value of the peptide having LH-RH activity, which is only sparingly absorbed from the digestive tract and has so far been used only by injections.

Aside from the above evaluations in terms of pharmacological effect, the absorption of LH-RH and the sustained activity thereof following a vaginal administration were studied by radioimmunoassay of serum LH. This experiment is described below as Example 7.

EXAMPLE 7

50 ng of the same peptide as that described in Example 5 was dispersed in an oleaginous base (composed predominantly of glyceryl trilaurate) in which 10% of citric acid had been previously incorporated. The serum LH level was then determined by radioimmunoassay. The results are set forth in Table 3.

Table 3

Changes in serum LH concentrations following a single intra-vaginal administration in diestrous rats

| Minutes after administration | serum LH concentration (mean ng/ml ±S.E.) |
|---|---|
| 0 | 23.8 ± 9.1 |
| 10 | 46.5 ± 7.8 |
| 20 | 59.7 ± 12.0 |
| 40 | 110.0 ± 16.4 |
| 60 | 178.0 ± 83.4 |
| 120 | 602.0 ± 254.9 |
| 180 | 166.6 ± 97.5 |
| 240 | 380.0 ± 182.4 |
| 300 | 158.6 ± 78.8 |
| 360 | 39.0 ± 9.1 |

5 rats were used in each group.
S.E. = standard error.

Thus, when 50 ng of the peptide of Example 5 was vaginally administered, a peak LH concentration which is 25 times as high as the normal level was obtained and, even 5 hours after administration, a level about 7 times as high as the pre-administration level was still retained. There are many reports suggesting that, as far as ovulation-stimulating activity is concerned, not only the levels of LH and FSH peaks but also the durability of adequate concentrations is a very important factor.

It is thus clear that the use of such a vaginal suppository containing a certain organic acid dispenses with the pain and trouble accompanying prolonged intravenous instillation or frequent intramuscular or subcutaneous injections and enables us to obtain the expected therapeutic effect with comparatively small amounts of the peptide having LH–RH activity.

EXAMPLE 8

Ten(10) grams of acid-treated gelatin was soaked overnight in 10 g of a 5% aqueous solution of citric acid (pH 3.5) (pH adjusted with a small amount of concentrated aqueous NaOH; hereinafter Solution A) whereby the gelatin was well swollen. Then, with the addition of 20 g of glycerin, the swollen gelatin was melted by heating to 60° C. A 33.3 g portion of this glycero-gelatin was weighed and 27.8 g of glycerin and 33.9 ml of the above Solution A were added. The mixture was stirred to homogeniety at 60° C. When a homogeneous mixture had been obtained, 5 ml of Solution A containing 83 to 533 mg of synthetic peptide having the formula (Pyr)-Glu-His-Trp-Ser-Tyr-Gly-Leu-Arg-Pro-Gly-$NH_2$ was added. The mixture was melted to homogeniety at 60° C., cast into molds and quenched. By the above procedure was obtained vaginal preparations (pH 3.5) for rats which contained 50 to 200 μg of peptide, each dosage unit weighing 60 mg.

EXAMPLE 9

1.5 g of gum xanthane was dispersed in 47 ml of Solution A and the dispersion was stirred to homogeniety at about 90° C. Separately, 1.5 g of locust bean gum was similarly dispersed in 45 ml of Solution A and stirred to homogeniety at about 90° C. The two fluids were mixed at about 90° C. to prepare a homogeneous gel. Under heating at 70°–80° C., a solution of 20 to 100 μg of peptide [monoacetate.pentahydrate.(Pyr)Glu-His-Trp-Ser-Tyr-D-Leu-Leu-Arg-Pro-NH-$C_2H_5$] in 5 ml of Solution A was added to the above homogeneous gel and the mixture was thoroughly stirred until a homogeneous gel (pH 3.5) was obtained. 100 mg of this gel was filled into an applicator to prepare a vaginal preparation for the rat.

EXAMPLE 10

50 ml of Solution A in which 0.12% of methylparaben and 0.012% of propylparaben had been dissolved (hereinafter, thus obtained solution is called Solution B) was heated to about 80° to 90° C. and 5 g of methyl-cellulose (Methorose ® 90 SH 4000, Shin-etsu Kagaku, Japan) was added and dispersed well with stirring. Separately, 1 g of synthetic peptide having the formula (Pyr)Glu-His-Trp-Ser-Tyr-D-Ala-Leu-Arg-Pro-NH-$C_2H_5$ was dissolved in 45 ml of Solution B and cooled (about 4°–10° C.). This cooled solution was added to the above dispersion and the mixture was stirred well at room temperature until a homogeneous gel was obtained. To compensate for the water lost by evaporation during this operation, a sufficient amount of distilled water was added to make a total of 100 g. Thereafter, the gel (pH 3.5) was centrifuged, defoamed and filled into a tube which was then sealed. One gram of this gel was dispensed into plastic vaginal inserters to prepare aqueous vaginal dosage units for human use, each containing 10 mg of the peptide.

EXAMPLE 11

250 mg of synthetic peptide having the formula (Pyr)Glu-His-Trp-Ser-Tyr-Gly-Leu-Arg-Pro-NH-$C_2H_5$ was accurately weighed and dissolved in an aqueous solution containing 0.12% of methylparaben, 0.012% of propylparaben and 3.0% of succinic acid (previously adjusted to pH 3.0 with a small amount of 10N-NaOH) to make a total of 100 ml. A one-ml portion of this solution (pH 3.0) was then supported by sorption on a glutaldehyde-treated porous collagen matrix in a plastic applicator to prepare a vaginal dosage unit containing 2.5 mg of the peptide.

EXAMPLE 12

A synthetic peptide (monoacetate.pentahydrate; (Pyr)Glu-His-Trp-Ser-Tyr-D-Leu-Leu-Arg-Pro-NH-$C_2H_5$) was dissolved in aliquots of Clark-Lubs buffer [J. Bact. 2, (1), 109, 191(1971) [or Sörensen's buffer [Ergeb.Physiol. 12, 3931 (1912)] at pH 2–7 and each solution was supported on a piece (substantially-predetermined volume) of cotton and administered into the vaginas of rats to investigate the pH dependence of the ovulation-stimulating activity of the peptide.

Using matured female SD rats (120–150 days, body weights from 250 to 350 g), each preparation was vaginally administered during the diestrus and the animal was autopsied next morning to check for the occurrence of ovulation based on the presence or absence of ova in the ampulla.

The results are shown in Table 4.

It will be apparent from Table 4 that the vaginal absorption of the peptide is pH-dependent. Thus, as the pH of the dosing solution was altered from 6.70 to 2.02, the $ED_{50}$ value was reduced to 1/4.5, thus showing that a significantly higher absorption can be obtained by making the solution acidic.

Table 4

| pH of dosing solution | Dose (ng/100 g body weight of rat) | | | | | | | | $ED_{50}$(ng/100g of rat) (95% fiducial limits) |
|---|---|---|---|---|---|---|---|---|---|
| | 20 | 30 | 40 | 50 | 60 | 80 | 100 | 150 | 200 | |
| 6.70 | | | | | | 0/10 | 4/10 | 4/10 | 8/10 | 144(115–201) |
| 4.76 | | | 4/20 | 12/20 | 13/20 | 15/20 | 15/15 | | | 52(44–58) |
| 3.47 | | | 0/10 | 2/10 | 3/13 | 8/10 | 5/5 | | | 67(60–79) |
| 2.02 | 2/10 | 5/10 | 6/10 | 7/10 | 10/10 | | | | | 32(23–40) | n/n: the number of ovulating rats/the number of vaginally dosed rats.
Note:
The solvent used in the preparation of solutions pH 6.7 and pH 4.76 was Clark-Lubs buffer. The solvent for solutions pH 3.47 and pH 2.02 was Sorensen's buffer.

EXAMPLE 13

The same peptide as that used in Example 12 was dissolved in 0.238 mol/liter aqueous solutions of various water-soluble aliphatic carboxylic acids which had been previously adjusted to pH 3.5 with small amounts of 10

N—NaOH. By the same procedure as that described in Example 12, rats were vaginally dosed with 0.2 ml/kg each of the solutions (pH 3.5) at a dose level of 40 ng/100 g to study the influence of those acids upon ovulation-stimulating activity.

The results are set forth in Table 5.

Table 5

| Organic carboxylic acid added | The number of ovulating rats/the number of vaginally dosed rats (40 ng/100 g body weights of rat) |
|---|---|
| None | 0/10 |
| Citric acid | 9/10 |
| Tartaric acid | 2/10 |
| Succinic acid | 10/10 |
| Malonic acid | 7/10 |
| Acetic acid | 5/10 |
| Malic acid | 3/10 |

The results showed that those aliphatic carboxylic acids assisted considerably in the absorption of the active peptide.

Then, an experiment was carried out to investigate the influence of the level of addition using citric acid as an example.

EXAMPLE 14

The same peptide as used in Example 12 was employed as the active component. Citric acid was added to aliquots of phthalate buffer (pH 3.5) at the levels of addition of 1, 2, 5, 7 and 10% (W/V) and the pH of each solution was readjusted to pH 3.5 with a small amount of concentrated NaOH. This solution was vaginally administered into rats in the same manner as Example 12 to investigate the influence of different levels of addition of citric acid upon ovulation-stimulating activity.

The results are shown in Table 6.

Table 6

| % concentration of citric acid in dosing solution | Dose (ng/100 g body weight of rat) | | | | | | | | $ED_{50}$ (ng/100g body weight of rat) (95% fiducial limits) |
|---|---|---|---|---|---|---|---|---|---|
| | 10 | 20 | 30 | 40 | 50 | 60 | 80 | 100 | |
| 0 | | | | 0/10 | 2/10 | 3/13 | 8/10 | 5/5 | 67(60–79) |
| 1 | | 0/10 | 1/10 | 6/10 | 5/10 | 8/10 | | | 44(37–54) |
| 2 | | 1/10 | 2/10 | 4/10 | 4/10 | 6/10 | | | 53(40–177) |
| 5 | 1/10 | 4/10 | 6/10 | 9/10 | | | | | 23(16–31) |
| 7 | 0/10 | 5/10 | 9/10 | | | | | | 20(15–25) |
| 10 | 2/10 | 7/10 | 10/10 | | | | | | 15(10–19) | n/n: The number of ovulating rats/the number of vaginally dosed rats

The above results showed that the absorption of said peptide following vaginal administration increased as citric acid, a polybasic organic acid, was added in increasing amounts.

The solutions containing 1 to 5% of citric acid were made isotonic with NaCl.

The results obtained in Examples 12, 13 and 14 have shown that the vaginal absorption of a peptide having LH-RH activity can be considerably increased by adjusting the pH of its solution acidic and adding a certain type of organic acid to the solution.

Thus, comparison of the ovulation-stimulating activities of said peptide by various routes of administration showed that its $ED_{50}$ values were 3.8 ng/100 g (body weight of rat) by the intravenous route, 5.8 ng/100 g (body weight of rat) by the subcutaneous route and 9.9 ng/100 g (body weight of rat) when an aqueous solution supplemented with 10% citric acid at pH 2.0 was vaginally administered. Thus, to achieve a given ovulation-stimulating activity, the vaginal preparation according to this invention requires only 2.6 times as much of peptide as by the intravenous route and 1.7 times as much of peptide as by the subcutaneous route. The unusual effectiveness of the vaginal preparation of this invention will also be apparent in view of the fact that oral administration requires 1900 times as much of peptide as by the intravenous route, rectal administration requires 82 times the dosage by the intravenous route, and vaginal administration with the oleaginous basis (Witepsol ® S55) requires 26 times as much of peptide as by the intravenous route.

In consideration of practical applications, an aqueous solution of the peptide similar to that used in Example 12 was dispersed in aliquots of various water-soluble gels and the ovulation-stimulating effect of each dispersion was determined to evaluate the absorption characteristic.

EXAMPLE 15

Using the same peptide as that used in Example 12 and various water-soluble gels, vaginal preparations were prepared by the procedures described in Examples 12, 13 and 14 as well as by procedures analogous thereto and each preparation was administered into the vaginas of rats by means of a glass applicator at the dose levels of 60 to 100 mg. The ovulation-stimulating effects were investigated by the same procedure as that described in Example 12.

The results are set forth in Table 7.

It will be apparent that satisfactory results were invariably obtained, although the absorption of peptide varied somewhat with different gel bases employed.

Table 7

| Base | | Dose (ng/rat) | | | | | | | | | $ED_{50}$ (ng/rat) (95% fiducial limits) |
|---|---|---|---|---|---|---|---|---|---|---|---|
| | | 30 | 40 | 50 | 60 | 70 | 80 | 100 | 120 | 150 | 200 | |
| Gum Xanthane | 3% | 1/10 | 3/10 | 7/10 | 8/10 | | | 9/9 | | | | 45(38–54) |
| methyl-cellulose | 5% | | | 1/10 | 2/10 | 3/10 | 8/10 | 9/10 | | | | 75(67–86) |
| Glycero-gelatin | 33% | | | | | | 0/10 | 2/10 | | 4/15 | 6/9 | 179(145–349) |
| CMC-Na | 5% | | | | | | | 1/7 | | 5/5 | | |
| Carrageenin | 5% | | | 2/5 | | | 5/5 | 5/10 | | 9/10 | | |
| Polyacrylic acid | 5% | | | | | | | 1/5 | | 2/5 | | |

Table 7-continued

| Base | | 30 | 40 | 50 | 60 | Dose (ng/rat) 70 | 80 | 100 | 120 | 150 | 200 | ED$_{50}$ (ng/rat) (95% fiducial limits) |
|---|---|---|---|---|---|---|---|---|---|---|---|---|
| Agar | 10% | | | 0/5 | | | | 4/5 | | | | |
| Starch | 10% | | | 1/10 | | | | 5/5 | | | | |
| CMC-glycerin | 5% | | | | | | | 1/5 | | | | | n/n: The number of ovulating rats/the number of vaginally dosed rats

EXAMPLE 16

The same peptide as that used in Example 12 was dissolved in a buffer containing 10% of citric acid (pH 2.0) and, after the solution (pH 2.0) was vaginally administered in the same manner as Example 12, the concentration of LH in the serum was determined by radioimmunoassay at timed intervals. As control, a solution of the same peptide in physiological saline was administered by the subcutaneous and intravenous routes, respectively, and the serum LH concentrations were measured in the same manner as above. In all cases, the dose was equal to the ED$_{50}$ value for ovulation-stimulating effect.

The results are shown in Table 8.

Table 8

Changes in serum LH concentrations following a single administration of the peptide in diestrous rats (mean ng/ml ± S.E.)

| Minutes after administration | s.c. 5.8 ng/100 g b.w. | i.v. 3.8 ng/100 g b.w. | Intra-vagina, buffer in cotton ball + 5% citric acid, pH 2, 9.9 ng/100 g. b.w. |
|---|---|---|---|
| 0 | 27.2 ± 2.7 (21 rats) | 27.2 ± 2.7 (21 rats) | 27.2 ± 2.7 (21 rats) |
| 10 | 40.9 ± 5.3 | 116.5 ± 8.2 | 30.4 ± 5.5 |
| 20 | 78.5 ± 15.1 | 90.5 ± 16.6 | 35.2 ± 7.1 |
| 40 | 138.0 ± 19.3 | 120.5 ± 16.0 | 28.0 ± 2.5 |
| 60 | 297.0 ± 89.5 | 323.5 ± 51.4 | 76.4 ± 21.3 |
| 120 | 561.0 ± 68.5 | 208.5 ± 24.9 | 648.0 ± 207.5 |
| 180 | 170.0 ± 50.6 | 46.6 ± 9.4 | 628.0 ± 137.2 |
| 240 | 4.1 ± 10.0 | 35.9 ± 7.9 | 357.0 ± 89.0 |
| 300 | 25.8 ± 4.9 | 41.8 ± 18.4 | 93.0 ± 11.9 |
| 360 | 56.1 ± 19.3 | 43.0 ± 13.6 | 71.1 ± 8.5 |

5 rats were used in each group.
s.c. = subcutaneously
i.v. = intraveneously
b.w. = body weight It will be apparent that, even though the ovulation-stimulating effects are comparable, the vaginal preparation according to this invention produces a serum LH level which has a higher peak and is significantly more sustained than it is the case when the subcutaneous or intravenous route is employed.

LH-RH and synthetic LH-RH derivatives invariably have very short biological half-lives in the body but the use of the dosage form according to this invention which, thus, permits continued administration, makes for a sustained blood level by a single dose and, hence, permits potentiation of LH-RH activity. The vaginal preparation according to this invention is also particularly effective in certain applications, for example when antitumour effects are desired, where LH-RH activity must be maintained over a prolonged time.

What we claim is:

1. A preparation for vaginal administration which contains 0.0001 to 5 percent by weight of a peptide having LH-RH activity homogeneously dispersed in an oleaginous or aqueous base, said preparation further containing homogeneously dispersed therein a water-soluble aliphatic polybasic carboxylic acid of 2 to 6 carbon atoms said polybasic carboxylic acid being present in an amount within the range of about 2 to 20 percent by weight when the preparation contains oleaginous base, or within the range of about 1 to 10 percent by weight when the preparation contains an aqueous base.

2. A preparation as claimed in claim 1, wherein the base is an oleaginous base.

3. A preparation as claimed in claim 1, wherein the base is an aqueous base.

4. A preparation as claimed in claim 3, wherein the pH of the preparation is 2 to 6.

5. A preparation as claimed in claim 1, wherein the peptide having LH-RH activity is of the formula:

(Pyr)Glu-R$_1$-Trp-Ser-R$_2$-R$_3$-R$_4$-Arg-Pro-R$_5$ wherein R$_1$ represents His, Tyr, Trp or p-NH$_2$-Phe, R$_2$ represents Tyr or Phe, R$_3$ represents Gly or a D-amino acid residue, R$_4$ represents Leu, Ile or Nle, R$_5$ represents (1) Gly-NH-R$_6$ wherein R$_6$ is H, lower alkyl or lower alkyl substituted by hydroxy or (2) NH-R$_6$ wherein R$_6$ is as previously defined.

6. A preparation as claimed in claim 5, wherein the peptide having LH-RH activity is
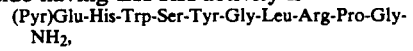
(Pyr)Glu-His-Trp-Ser-Tyr-Gly-Leu-Arg-Pro-Gly-NH$_2$,

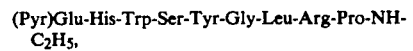
(Pyr)Glu-His-Trp-Ser-Tyr-Gly-Leu-Arg-Pro-NH-C$_2$H$_5$,

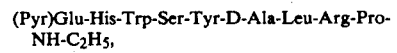
(Pyr)Glu-His-Trp-Ser-Tyr-D-Ala-Leu-Arg-Pro-NH-C$_2$H$_5$, or

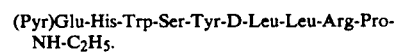
(Pyr)Glu-His-Trp-Ser-Tyr-D-Leu-Leu-Arg-Pro-NH-C$_2$H$_5$.

7. A preparation as claimed in claim 1, wherein the polybasic carboxylic acid is, a member selected from the group consisting of a dicarboxylic acid and a tricarboxylic acid.

8. A preparation as claimed in claim 7, wherein the dicarboxylic acid is selected from the group of succinic acid, tartaric acid, malonic acid, glutaric acid, malic acid and aspartic acid.

9. A preparation as claimed in claim 7, wherein the tricarboxylic acid is citric acid.

* * * * *